(12) United States Patent
Kristiansson et al.

(10) Patent No.: US 7,375,345 B2
(45) Date of Patent: May 20, 2008

(54) EXPOSED CONDUCTOR SYSTEM AND METHOD FOR SENSING AN ELECTRON BEAM

(75) Inventors: Anders Kristiansson, Lund (SE); Lars-Åke Näslund, Furulund (SE); Hans Hallstadius, Lund (SE); Anders Hedse Olsson, Staffanstorp (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 225 days.

(21) Appl. No.: 11/258,212

(22) Filed: Oct. 26, 2005

(65) Prior Publication Data
US 2007/0114432 A1 May 24, 2007

(51) Int. Cl.
*H01J 33/04* (2006.01)
(52) U.S. Cl. ................................ 250/397; 250/492.3
(58) Field of Classification Search ............. 250/397, 250/492.3
See application file for complete search history.

(56) References Cited

U.S. PATENT DOCUMENTS

| | | |
|---|---|---|
| 3,056,059 A | 9/1962 | Hermsen |
| 3,338,653 A | 8/1967 | Anton |
| 4,644,167 A | 2/1987 | Sorber |
| 5,644,220 A * | 7/1997 | Urs et al. ............... 324/71.3 |
| 6,657,212 B2 | 12/2003 | Komori et al. |
| 2004/0119024 A1 | 6/2004 | Avnery |

FOREIGN PATENT DOCUMENTS

| | | |
|---|---|---|
| DE | 20 47 593 A1 | 3/1972 |
| DE | 44 29 925 C1 | 11/1995 |
| EP | 0 174 691 A1 | 3/1986 |
| EP | 0 234 821 A2 | 9/1987 |
| EP | 0 239 808 A1 | 10/1987 |
| GB | 606013 A | 8/1948 |
| GB | 2337108 A | 11/1999 |
| WO | WO 8603332 A1 | 6/1986 |
| WO | WO2004/061890 A2 | 7/2004 |

OTHER PUBLICATIONS

PCT Search Report - PCT/SE2006/001146 - dated Feb. 23, 2007.
PCT Search Report - PCT/SE2006/001147 - dated Feb. 23, 2007.
PCT Written Opinion - PCT/SE2006/001147 - dated Feb. 23, 2007.
UK Search Report - GB 9910565.2 - dated Jul. 12, 1999.

* cited by examiner

*Primary Examiner*—Kiet T. Nguyen
(74) *Attorney, Agent, or Firm*—Buchanan Ingersoll & Rooney PC

(57) ABSTRACT

A detector is disclosed for sensing an intensity of an electron beam generated along a path. An exemplary detector includes an exposed conductor attached to a support which is configured to locate the exposed conductor within a path of an electron beam; a grounded conductor isolated from the exposed conductor, the grounded conductor partly surrounding the exposed conductor to form a plasma shield having a window positioned at least in a direction of the electron beam path.

35 Claims, 4 Drawing Sheets

EXPOSED CONDUCTOR SYSTEM AND METHOD FOR SENSING AN ELECTRON BEAM

BACKGROUND

Electron beams are used in a variety of applications including, but not limited to irradiation of packaging materials for sterilization purposes. For example, packaging materials such as cartons used to hold liquids for human consumption are sterilized using electron beam irradiation. To provide on-line control of the intensity of the electron beam, and to monitor uniformity variations, electron sensors are used for dose irradiation measurement. A signal from the sensor is analyzed and fed back into an electron beam control system as a feedback control signal. In the sterilization of packaging material, such sensor feedback can be used to assure a sufficient level of sterilization. Different levels of sterilization can be chosen depending on how long shelf-life is desired and whether the distribution and storage of the packages is made in chilled or ambient temperature.

One kind of existing sensor for measuring electron beam intensity, based on direct measuring methods, uses a conductor placed within a vacuum chamber. The vacuum chamber is used to provide isolation from the surrounding environment. Because vacuum-based sensors can be relatively large, they are located at positions outside the direct electron beam path to avoid shadowing of target objects. Shadowing can, for example, preclude proper irradiation (and thus, proper sterilization) of packaging material. Therefore, these sensors rely on secondary information from a periphery of the beam, or information from secondary irradiation, to provide a measurement.

In operation, electrons from the electron beam which have sufficient energy will penetrate a window, such as a titanium (Ti) window of the vacuum chamber and be absorbed by the conductor. The absorbed electrons establish a current in the conductor. The magnitude of this current is a measure of the number of electrons penetrating the window of the vacuum chamber. This current provides a measure of the intensity of the electron beam at the sensor position.

A known electron beam sensor having a vacuum chamber with a protective coating, and an electrode representing a signal wire inside the chamber, are described in published U.S. patent application No. US 2004/0119024. The chamber walls are used to maintain a vacuum volume around the electrode. The vacuum chamber has a window accurately aligned with the electrode to sense the electron beam density. The sensor is configured for placement at a location, relative to a moving article being irradiated, opposite the electron beam generator for sensing secondary irradiation.

A similar electron beam sensor is described in patent publication WO 2004 061890. In one embodiment of this sensor, the vacuum chamber is removed and the electrode is provided with an insulating layer or film. The insulating layer is provided to avoid influence from electrostatic fields and plasma electrons created by the electron beam from substantially influencing the electrode output.

U.S. Pat. No. 6,657,212 describes an electron beam irradiation processing device wherein an insulating film is provided on a conductor, such as a stainless steel conductor, of a current detection unit placed outside a window of an electron beam tube. A current measuring unit includes a current meter that measures current detected. This patent describes advantages of a ceramic coated detector.

SUMMARY

A detector is disclosed for sensing an intensity of an electron beam generated along a path. An exemplary detection includes an exposed conductor attached to a support which is configured to locate the conductor within a path of an electron beam; a second conductor isolated from the exposed conductor, the second conductor being connected to a voltage potential and partly surrounding the exposed conductor to form a plasma shield, the plasma shield having a window by which the exposed conductor is exposed to the electron beam, the window being positioned at least in a direction of the electron beam path.

An apparatus is disclosed for sensing an intensity of an electron beam generated along a path. The exemplary apparatus includes means for conducting a current established by electrons of the electron beam; and means for shielding the conducting means from plasma, the shielding means having an open window located to directly expose at least a portion of the conducting means to a path of the electron beam.

A detector is disclosed for sensing an intensity of an electron beam generated along a path. An exemplary detector includes an exposed conductor attached to a support which is configured to locate the conductor within a path of an electron beam; and a second conductor isolated from the exposed conductor and positioned to impact an influence of secondary electrons on the exposed conductor by substantially limiting exposure of said conductor to at least the direction of the electron beam path.

A method is disclosed for irradiating a target area with an electron beam emitted along a path. An exemplary method is disclosed for emitting an electron beam through an electron exit window and along a path; detecting the electron beam exiting the electron exit window, the detecting being performed using an exposed conductor and a second conductor isolated from the exposed conductor, the second conductor partly surrounding the exposed conductor to form a plasma shield having a window positioned at least in a direction of the electron beam path; and maintaining a moving target material at a desired measuring position relative to the exposed conductor.

BRIEF DESCRIPTION OF THE DRAWINGS

Other features and embodiments will become apparent to those skilled in the art upon reading the following detailed description of preferred embodiments, in conjunction with the accompanying drawings, wherein like reference numerals have been used to designate like elements, and wherein.

DETAILED DESCRIPTION

Figure 1:
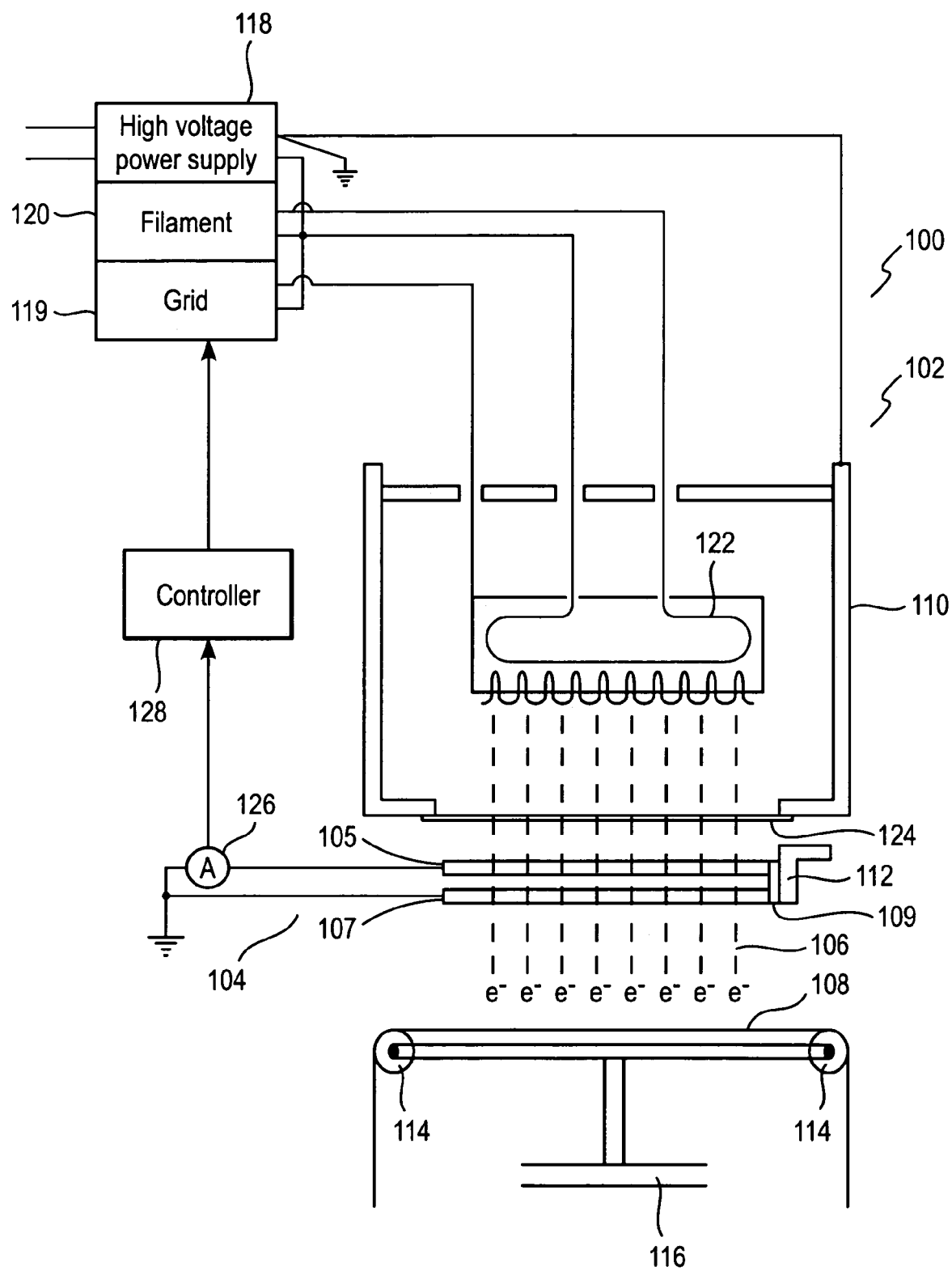
FIG. 1 shows an exemplary system for irradiating a target area with an electron beam in accordance with an exemplary embodiment.

FIG. 1 shows an apparatus, represented as an exemplary system 100, for irradiating a target area within an electron beam emitted along the path. The system 100 can include an apparatus, such as a detector 104, for sensing an intensity of an electron beam generated along a path. The detector 104 can include a means, such as an exposed conductor 105, for conducting a current established by electrons of the electron beam. In an exemplary embodiment, the exposed conductor 105 is attached to a support 112 which is configured to locate the conductor within a path of an electron beam 106.

The detector 104 can also include a means, such as a second conductor 107, for shielding the conducting means from plasma, the shielding means having a window located to expose the conducting means to a path of the electron beam. The second conductor 107 can be isolated from the exposed conductor 105, and can be configured to partly surround the exposed conductor to form a plasma shield. The plasma shield can, for example, include a window by which at least a portion of the exposed conductor is directly exposed to the electron beam, the window being positioned at least in a direction of the electron beam path.

In an exemplary embodiment, the second conductor 107 is connected to a voltage potential such as a ground potential of the detector (e.g., a ground potential of the exemplary system 100), or is connected to a voltage potential sufficient to impact a rate at which electrons are drawn from plasma in a vicinity of the detector.

As referenced herein, such a rate can be determined empirically by adjusting the voltage applied to the second conductor until a desired level of consistency and accuracy in the measurement of the electron beam intensity is achieved over a specified period of time. During this specified period of time, the electron beam intensity can be monitored, for example, by connecting the second conductor to a test potential, and by simultaneously using a second independent detector (configured similar to the detector of FIG. 1, or other suitable configuration, with its outer layer at ground potential). The second detector can be periodically placed in the electron beam path over the specified period of time to measure the electron beam intensity during a setup phase. The second detector, when periodically inserted into the electron beam path, can be used to obtain a measurement which is compared against the measurement obtained using the FIG. 1 detector (which is continuously maintained within the electron beam path). Between measurements, the second detector can be removed from the electron beam path and any plasma buildup can be discharged. The voltage potential on the FIG. 1 detector can be adjusted over different setup phase cycles until a voltage potential applied to the second conductor is identified which provides a desired consistency and accuracy of the FIG. 1 detector measurements. In an exemplary embodiment, a voltage potential on the order of 0 to 10 volts can be applied to the second conductor.

In the FIG. 1 embodiment, the second conductor 107 is positioned below the conductor 105 such that the "window" is formed by an exposed portion of conductor 105 which is not directly facing the second conductor 107. Additional exemplary embodiments of the window will be discussed later with respect to FIG. 4. The second conductor 107 is isolated from the exposed conductor and positioned to impact an influence of secondary electrons on the exposed conductor by substantially limiting exposure of the exposed conductor to at least a direction of the electron beam path.

The exemplary detector 104 can be used in combination with other portions of the FIG. 1 system 100. In FIG. 1, the system 100 includes means for emitting electrons, such as an electron beam generator 102, for emitting the electron beam 106 along a path. A means, such as support 114, is provided for supporting a target material in a target area 108. The detector 104 can be used for sensing an intensity of an electron beam 106 generated by the electron beam generator along a path which irradiates a target area 108.

The electron beam generator 102 for emitting an electron beam 106 along a path includes a vacuum chamber 110. The support 112 is provided to hold the electron beam detector at a position along the path between the vacuum chamber and the target area. The detector 104 is insulated from the support 112 via an insulator 109. The electron beam detector 104 can be formed with an exposed conductor located at a position along the path between the vacuum chamber 110 and the target area 108 to detect and momentarily measure the intensity of the electron beam 106 exiting the vacuum chamber.

The support 114 which is provided for supporting a target material within a vicinity of the target area 108 can be associated with, for example, a packaging material fixing device 116. In an exemplary embodiment, the support 114 for the target material can be a packaging material web transport roller or any other suitable device. The support 114 can be used to hold the target material in the target area at a desired measuring position relative to the exposed conductor of the electron beam detector 104.

The desired measuring position can, for example, be a position which is a stable distance from the exposed conductor. Alternatively, it can be a position which is a controlled, repeatable varying distance from the exposed conductor. As such, the desired measuring position can be one of multiple conditions as a target material is moved in and about a vicinity of the electron beam 106.

The support 112 for the electron beam detector 104 can be configured to locate the detector between the electron beam generator and the target area 108, within a direct path of an electron beam to be generated by the electron beam generator 102. As referenced herein, the phrase "within a direct path" refers to a location between an electron beam output of an electron beam exit window and the target area, such that electrons all along a desired width of the beam 106 are sensed, and not just the electrons of a limited area. Electrons from the beam in parallel paths impact any target object placed in the target area 108.

The electron beam generator 102, as shown in the exemplary FIG. 1 embodiment, includes a high voltage power supply 118, suitable for providing sufficient voltage to drive the electrical beam generator for the desired application. The electron beam generator also includes a filament power supply 120 referenced to the high voltage of the high voltage power supply 118 with a suitable output voltage for an electron emitting filament 122 of the electron beam generator. In addition, the high voltage power supply includes a grid control 119.

The filament 122 can be housed in a reflector inside the vacuum chamber 110. In an exemplary embodiment, the vacuum chamber 110 can be hermetically sealed. In operation, electrons (e⁻) from the filament 122 are emitted along an electron beam path, such as the path along the electron beam 106, in a direction towards the target area 108.

In the exemplary FIG. 1 embodiment, the detector 104 is shown as being independent of the electron beam generator 102. The electron beam 106 generated by the filament 122 can pass through an electron exit window 124 of the electron beam generator.

Electrons which reach the electron beam detector 104 can be detected and measured. For example, a current meter 126 can be provided to measure electrical current in the exposed conductor of the electron beam detector 104, as a measure of electron beam intensity. An output from the current meter can be supplied to a controller 128, which can serve as a means for adjusting an intensity of the electron beam in response to an output of the electron beam detector. For example, the electron beam intensity can be regulated to a setpoint using feedback from the controller 128. In exemplary embodiments, the electron beam can be emitted with an energy of, for example, less than 100 keV or lesser or greater as desired (e.g., 60 to 80 keV).

The current meter 126 can be any device suitable for measuring an intensity of the electron beam either directly or indirectly. For example, the current meter can be a voltmeter in combination with a resistor, or an amperemeter, or any other suitable device.

The exemplary electron beam detector 104 includes an exposed conductor which can, for example, be formed as a bare wire probe. In an exemplary embodiment, the exposed conductor of the detector 104 can be a copper or stainless steel wire, or any other suitable conductor. To protect the wire from the environment it can be coated with a conductive coating. For example, the outer conductive coating can be an inert conductive material, such as gold or diamond.

The conductor, when introduced to the electron beam, can capture electrons which can be recorded as an electrical current representing a momentary measure of electron beam intensity. The conductor can be configured of relatively small dimension, to fit into any geometry.

When an electron emitted from the filament 122 of FIG. 1 travels toward the target area, it will collide with air molecules along this path. The emitted electrons can have sufficient energy to ionize the gas along this path, thereby creating a plasma which contains ions and electrons. Plasma electrons are secondary electrons, or thermal electrons, with low energy compared to the electrons from the electron beam. The plasma electrons have randomized vector velocity and can only travel a distance which length is a small fraction of the mean free path for the beam electrons.

Figure 2:
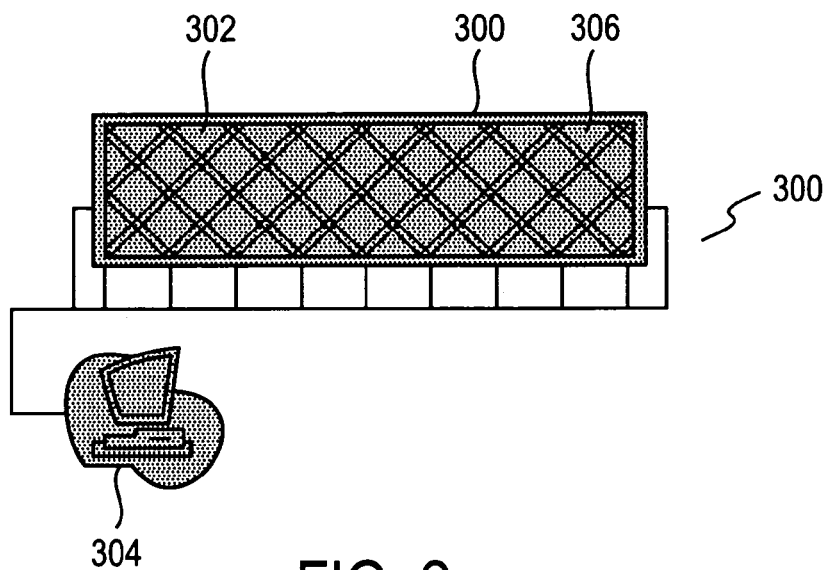
FIGS. 2 and 3A-3B show exemplary embodiments of multi-detector configurations.

In exemplary embodiments, the detector can be formed as a dose mapping unit. For example, FIG. 2 shows an exemplary embodiment wherein two dimensional measurements of electron beam intensity can be provided. Here, an exemplary array of detectors is formed as a grid to detect intensity of an electron beam at each of plural locations within two dimensions of a cross section of the electron beam path (that is, in a plane transverse to the electron beam path).

In the detector 300 of FIG. 2, an array of detectors 302 can be provided in a grid arrangement which can be attached to an electron exit window 306 The detector 300 can thus be considered as a mesh of detectors, or a dose mapping unit. Information from each conductor (e.g., signal amplitudes, signal differences/ratios, conductor positions and so forth), can be used to produce an emission intensity plot via a processor 304. In addition, the grid arrangement can function as a protection for the exit window 306.

In addition, in the exemplary FIG. 2 embodiment, detectors 302 can be arranged at angles to one another, and/or at angles relative to a desired transport direction of a target material in the target area, and in a plane transverse to the electron beam path. Such a configuration can result in minimal shadowing of a target material passing beneath the grid.

For example, where a target object, such as a packaging material, passes from a lower portion of the diagram in for example FIG. 2 to a top of the diagram, all portions of the packaging material will be equally irradiated by the electron beam as the material passes. The angled detectors will sense the electron beam at multiple locations across its two dimensional cross section, thereby providing an accurate plot of electron beam intensity without impacting the sterilization process. However, it should be understood that in an exemplary embodiment (not shown) the angle can as well be 0 or 90 degrees, i.e. the detector can be positioned at right angles to the electron exit window.

Figure 3A:
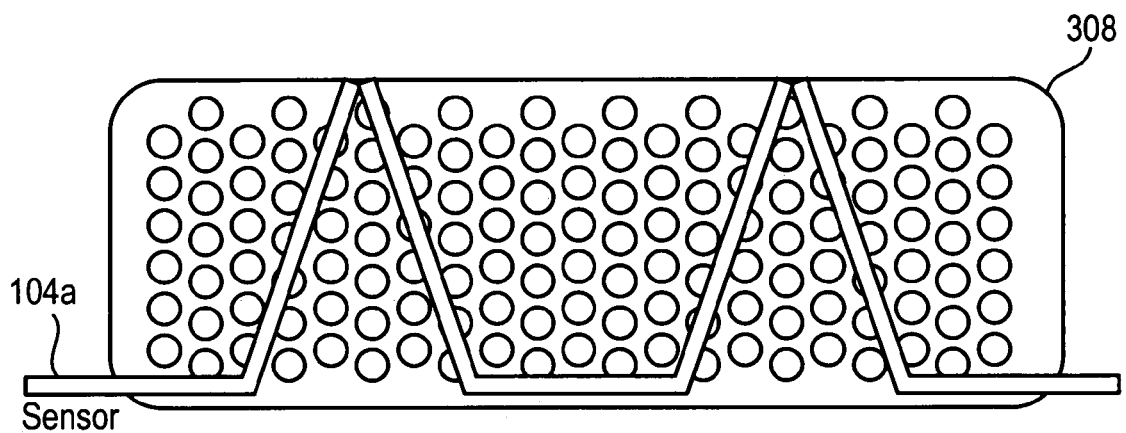
Figure 3B:
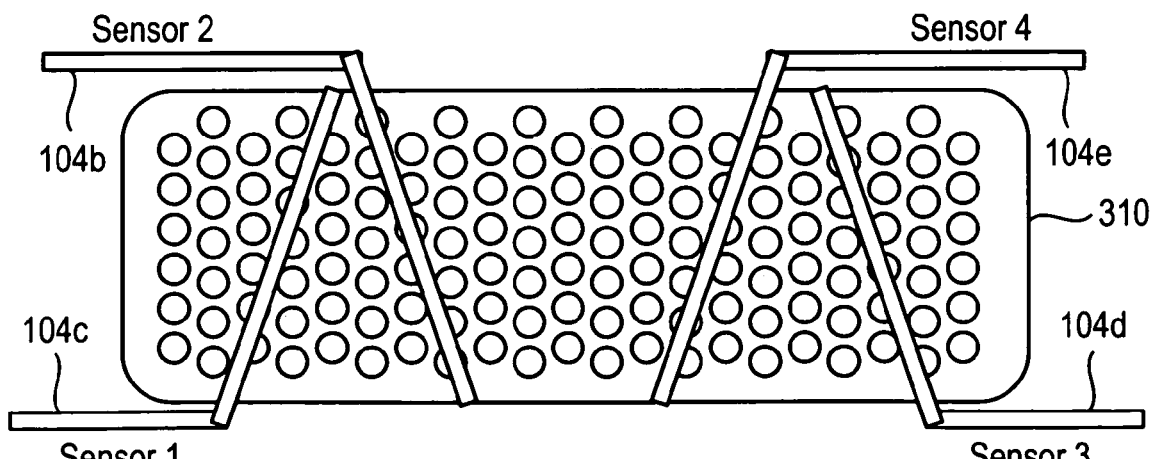

FIGS. 3A and 3B show exemplary embodiments wherein exit windows 308 and 310, respectively are formed as structures having honeycomb supports. The exit window can be formed using a foil supported on the honeycomb structure. The holes of the honeycomb structure allow the electron beam to pass from the vacuum chamber toward a detector 104a in FIG. 3A. In FIG. 3B, multiple detectors 104b, 104c, 104d and 104e are provided in a symmetrical arrangement. Any number of such detectors can, of course, be used. The detectors in these embodiments can as well function as a window protection.

FIGS. 4A-4K show yet additional embodiments of exemplary detectors. These detectors can be used in accordance with exemplary embodiments as the detector 104 of FIG. 1.

Figure 4A:
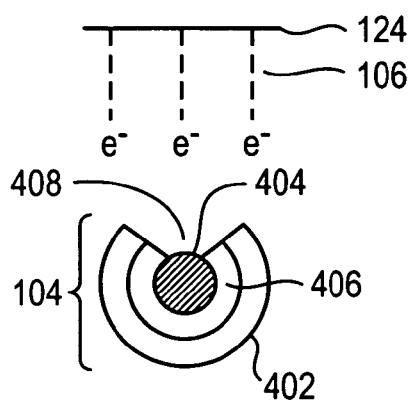
FIGS. 4A-4K show alternate embodiments of an electron beam detector.

In FIG. 4A, a detector is shown comprising an exposed conductor 404 which is used to detect the momentary intensity of the electrons in the electron beam. A second conductor 402 of the detector 104 is formed as an outer layer which is isolated from the exposed conductor 404 by an insulating layer 406. The second conductor 402 is connected to a voltage potential, such as ground potential or any other desired potential, in a manner as discussed with respect to the second conductor 107 of the FIG. 1 embodiment.

The second conductor 402, and the insulating layer 406, only partly surround the conductor 404 so that the conductor 404 is exposed via a window 408 at a desired shielding/exposure angle. In the exemplary embodiment described herein, the exposure angle is an angle that represents the portion of the conductor 404 which is directly exposed to the electron beam 106 (e.g., the beam emitted via the electron beam window 124).

In FIG. 4A, an exposed portion of the conductor 404 is approximately 60 degrees such that the shielding/exposure angle would be 300 degrees. Of course any suitable shielding/exposure angle can be used, including, but not limited to angles of 180 degrees or lesser or greater.

In the FIG. 4A embodiment, when the target material is positioned a stable distance from the conductor, plasma will not substantially affect the conductor and measurements of the electron beam intensity. The plasma will substantially be attracted to the target material and will not be captured by the conductor 404.

FIGS. 4A-4K show embodiments of a detector which can be used, for example, in cases where the distance of the detector to the target material fluctuates. These detectors can also be used, for example, for stable distances or distances that vary in a controlled manner.

Figure 4B:
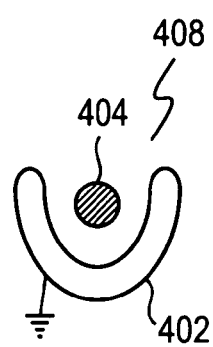

FIG. 4B shows an alternate embodiment that comprises an exposed conductor 404 and a second conductor 402 maintained at a voltage potential such as ground. The second conductor is formed with a U-shaped cross section, and as shown, a shielding/exposure angle of 180 degrees. The second conductor 402 is provided so that changes in the amount of plasma electrons close to the exposed conductor 404 will be superceded by the second conductor 402.

The second conductor 402 can be used to minimize impact of plasma on the current measurement and forms a shielding to the conductor 404, preventing it from being substantially affected by the surrounding plasma electrons. The plasma electrons will instead be attracted by the grounded conductor 402. In the embodiment shown in FIG. 4B air between the conductor 404 and the grounded conductor 402 serves as insulation. Alternative configurations to using a cylindrical conductor 404 will be apparent to those skilled in the art. For example, rather than a cylinder, a square conductor can be formed.

Figure 4C:
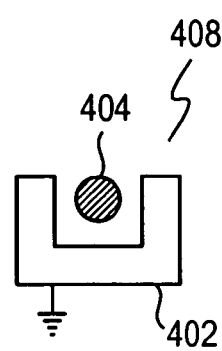

In FIG. 4C, the grounded conductor 402 is formed with a more squared off configuration, with a shielding/exposure angle of 180 degrees.

FIGS. 4D-4J, like FIG. 4A, include an insulating material between the exposed conductor 404 and the grounded conductor 402 as isolation. FIGS. 4D-4J show alternate configurations of the detector 104, wherein for illustration purposes, the shielding/exposure angle is 180 degrees.

Figure 4D:
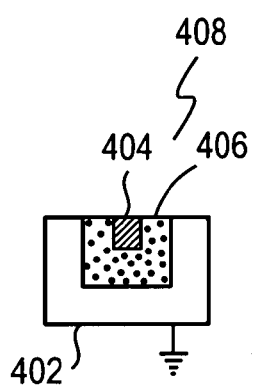

In FIG. 4D, more squared off cross sections are used for the exposed conductor 404 and the grounded conductor 402, and an insulating material 406 is provided between the two conductors.

Figure 4E:
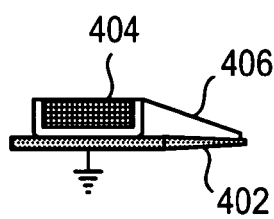

FIG. 4E shows a detector comprising an exposed conductor 404 having a rectangular cross section, and a second conductor formed as a grounded substrate 402, with an insulating member 406 therebetween.

Figure 4F:
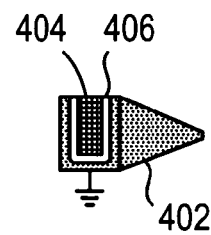

FIG. 4F shows a similar configuration, wherein the substrate 402 is formed to match the shape of the insulating layer 406 and the exposed conductor 404.

Figure 4G:
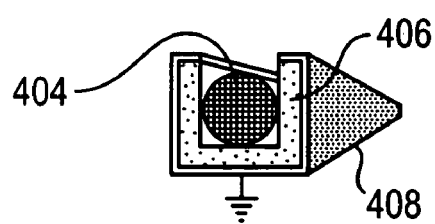

In FIG. 4G, an arrangement of FIG. 4F is used with a cylindrical exposed conductor 402. In FIG. 4G, note that the second conductor 402 encompasses an upper surface of the insulting layer 406 facing the electron beam generator.

Figure 4H:
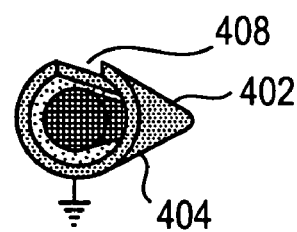

In FIG. 4H, a cylindrically shaped exposed conductor and a grounded conductor are used, wherein the second conductor 402 has the window 408 formed as an opening in a direction facing the electron beam generator.

Figure 4I:
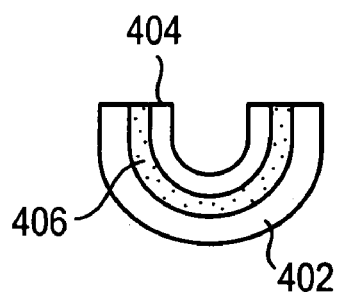

In FIG. 4I another embodiment is shown wherein the detector is formed as a sandwich with U-shaped cross section comprising an exposed conductor 404 and a second conductor 402 with an insulating layer 406 therebetween.

Figure 4J:
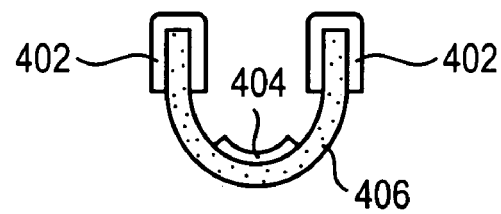

In FIG. 4J, an embodiment somewhat similar to that of Figure I is shown, in which the insulating layer 406 has a U-shaped cross section. The second conductor 402 is split in two portions, whereby each respective portion is provided on one U-leg end. The exposed conductor 404 is provided on the inner side of the U-shaped insulating layer and isolated from the second conductors 402.

Thus, in these configurations, at least a portion of the conductor 404 is directly exposed to the electron beam from the electron beam generator. Of course, those skilled in the art will appreciate that other configurations and shapes and selections of materials for the exposed conductor, second conductor, and insulating layer can be used. For example, the exposed conductor can be formed as a conductive surface of a substrate. In the same way the second conductor can be formed as a conductive surface of a substrate. The substrate can be an insulating layer, or member, to which both conductors are formed.

Figure 4K:
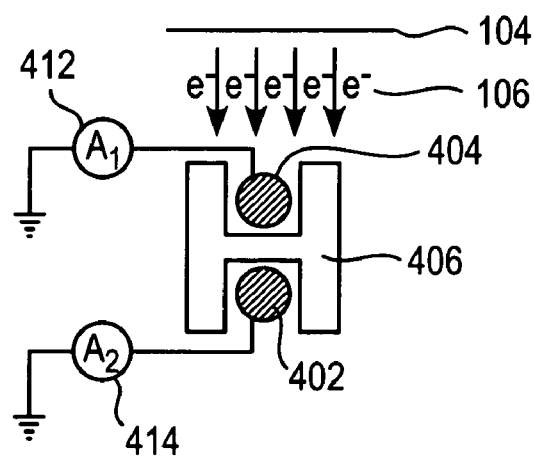

FIG. 4K shows an alternate embodiment wherein the exposed conductor 404 is included within an insulator formed as insulating layer 406 that is in an H-shaped configuration. The second conductor 402 is provided within a portion of the H-shaped insulating member 406, such that it is isolated from the exposed conductor 404, and is not directly exposed to the electron beam 106 emitted from, for example, an electron exit window 104. The conductors 402, 404 can be formed as bare wires.

Each of the exposed conductor 404 and the second conductor 402 can be connected to measuring devices, such as current meters 412 and 414 which produce outputs $A_1$ and $A_2$, respectively. The outputs from the current meters 412 and 414 can be supplied to the FIG. 1 controller 128. The electron beam intensity can be determined as a measure $A_1$-$A_2$, wherein $A_1$ is a current measure proportional to both electrons and plasma, while $A_2$ is a measure of plasma only. These measurements can also be used to determine electron beam intensity.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A detector for sensing an intensity of an electron beam generated along a path, comprising:
    an exposed conductor attached to a support which is configured to locate the second conductor within a path of an electron beam; and
    a second conductor isolated from the exposed conductor, the second conductor being connected to a voltage potential and partly surrounding the exposed conductor to form a plasma shield, the plasma shield having a window by which the exposed conductor is exposed to the electron beam, the window being positioned at least in a direction of the electron beam path.

2. Detector according to claim 1, wherein the second conductor is connected to ground potential of the detector.

3. Detector according to claim 1, wherein the second conductor is connected to a voltage potential sufficient to impact a rate at which electrons are drawn from plasma in a vicinity of the detector.

4. Detector according to claim 1, comprising:
    a current meter to detect electrical current in the exposed conductor as a measure of electron beam intensity.

5. Detector according to claim 1, wherein the exposed conductor is formed with an outer conductive coating.

6. Detector according to claim 5, wherein the outer conductive coating is an inert conductive material.

7. Detector according to claim 1, comprising:
    an array of exposed conductors to detect an intensity of the electron beam at each of plural locations within the path.

8. Detector according to claim 7, wherein the exposed conductors of the array are arranged at angles relative to a desired transport direction of a target material within a target area, and in a plane transverse to the path.

9. Detector according to claim 7, comprising:
    means for comparing a level of electrical current detected in at least two different exposed conductors as a measure of electron beam intensity.

10. Detector according to claim 1, wherein the exposed conductor is formed as a conductive surface of a substrate.

11. Detector according to claim 10, comprising:
    an array of exposed conductors each formed on a substrate to detect intensity of the electron beam at each of plural locations.

12. Detector according to claim 11, wherein the exposed conductors are arranged at angles relative to a desired transport direction of a target material within a target area, and in a plane transverse to the path.

13. Detector according to claim 1, comprising:
    an insulating member connected to a grounded conductor.

14. A detector according to claim 1, in combination with a system for irradiating a target area with an electron beam emitted along a path, comprising:
    an electron beam generator for emitting the electron beam along a path, wherein the electron beam generator includes an electron exit window, the detector being located at a position along the path between the electron generator and a target area to detect and measure an intensity of the electron beam exiting the electron exit window.

15. Detector according to claim 14, wherein the detector is applied on an exterior of the electron exit window.

16. Detector according to claim 14, comprising:
an electron beam controller to adjust intensity of the electron beam in response to an output of the electron beam detector.

17. Detector according to claim 14, wherein the electron beam is emitted with an energy of less than 100 keV.

18. Detector according to claim 14, comprising a support to hold target material in the target area, the support including:
at least one packaging material web transport roller.

19. Detector according to claim 1, comprising:
an insulator formed in an H-shaped configuration, wherein the exposed conductor and the second conductor are isolated from one another by the insulator.

20. A system, in combination with the detector according to claim 19, comprising:
a first sensor connected to the exposed conductor;
a second sensor connected to the second conductor; and
a processor for combining outputs of the first and second sensors as a measure of electron beam intensity.

21. Apparatus for sensing an intensity of an electron beam generated along a path, comprising:
means for conducting a current established by electrons of the electron beam; and
means for shielding the conducting means from plasma, the shielding means having a window located to directly expose at least a portion of the conducting means to a path of the electron beam.

22. Apparatus according to claim 21, in combination with:
means for emitting an electron beam along a path, the emitting means including an electron exit window; and
means for supporting a target material in a target area.

23. Apparatus according to claim 22, comprising:
means for measuring electrical current from the conducting means as a measure of electron beam intensity.

24. Apparatus according to claim 22, wherein the conducting means includes:
an array of exposed conductors to detect an intensity of the electron beam at each of plural locations within the path.

25. Apparatus according to claim 22, wherein the conducting means is formed as a conductive surface on a substrate.

26. Apparatus according to claim 22, comprising:
means for controllably adjusting an intensity of the electron beam in response to the intensity of the electron's beam.

27. A detector for sensing an intensity of an electron beam generated along a path, comprising:
an exposed conductor attached to a support which is configured to locate the conductor within a path of an electron beam; and
a second conductor isolated from the exposed conductor and positioned to impact an influence of secondary electrons on the exposed conductor by substantially limiting exposure of the exposed conductor to at least the direction of the electron beam path.

28. A detector according to claim 27, wherein the influence of secondary electrons on the exposed conductor is achieved by substantially limiting an exposure angle of said second conductor to exposure at least in the direction of the electron beam path.

29. A detector according to claim 27, comprising:
a current meter to measure electrical current in the exposed conductor as a measure of electron beam intensity.

30. A detector according to claim 27, comprising:
an array of exposed conductors to detect an intensity of the electron beam at each of plural locations within the path.

31. A detector according to claim 27, wherein the exposed conductor is formed as a conductive surface on a substrate.

32. A detector according to claim 27, wherein the detector is applied on an exterior of an electron exit window.

33. Method for irradiating a target area with an electron beam emitted along a path, comprising:
emitting an electron beam through an electron exit window and along a path;
detecting the electron beam exiting the electron exit window, the detecting being performed using an exposed conductor; and
a second conductor isolated from the exposed conductor, the second conductor partly surrounding the exposed conductor to form a plasma shield having a window positioned at least in the direction of the electron beam path; and
maintaining a moving target material at a desired measuring position relative to the exposed conductor.

34. Method according to claim 33, wherein the exposed conductor is located between the electron exit window and the target material.

35. Method according to claim 33, comprising:
measuring electrical current from the exposed conductor as a measure of electron beam intensity.

* * * * *